United States Patent
Fujii et al.

(10) Patent No.: US 10,092,536 B2
(45) Date of Patent: *Oct. 9, 2018

(54) SELF-EMULSIFYING COMPOSITION OF ω3 FATTY ACID

(71) Applicant: MOCHIDA PHARMACEUTICAL CO., LTD., Tokyo (JP)

(72) Inventors: Hirosato Fujii, Tokyo (JP); Motoo Yamagata, Tokyo (JP)

(73) Assignee: MOCHIDA PHARMACEUTICAL CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/409,315

(22) Filed: Jan. 18, 2017

(65) Prior Publication Data

US 2017/0119724 A1    May 4, 2017

Related U.S. Application Data

(60) Continuation of application No. 14/745,888, filed on Jun. 22, 2015, now Pat. No. 9,579,281, which is a division of application No. 14/069,718, filed on Nov. 1, 2013, now Pat. No. 9,089,483, which is a division of application No. 13/321,801, filed as application No. PCT/JP2010/058676 on May 21, 2010, now Pat. No. 8,618,168.

(30) Foreign Application Priority Data

May 22, 2009 (JP) ................. 2009-124444

(51) Int. Cl.
| | |
|---|---|
| A61K 31/00 | (2006.01) |
| A61K 31/202 | (2006.01) |
| A61K 31/232 | (2006.01) |
| A61K 47/46 | (2006.01) |
| A61K 47/44 | (2017.01) |
| A61K 47/10 | (2017.01) |
| A61K 47/26 | (2006.01) |
| A61K 9/107 | (2006.01) |

(52) U.S. Cl.
CPC ............ *A61K 31/232* (2013.01); *A61K 9/107* (2013.01); *A61K 47/10* (2013.01); *A61K 47/26* (2013.01); *A61K 47/44* (2013.01); *A61K 47/46* (2013.01)

(58) Field of Classification Search
CPC .... A61K 31/00; A61K 31/202; A61K 31/232; A61K 47/10; A61K 47/26; A61K 47/44; A61K 47/46; A61K 9/107; A61K 9/1075
See application file for complete search history.

(56) References Cited

U.S. PATENT DOCUMENTS

| | | |
|---|---|---|
| 5,567,730 A | 10/1996 | Miyashita et al. |
| 6,284,268 B1 | 9/2001 | Mishra et al. |
| 2006/0251685 A1 | 11/2006 | Yu et al. |
| 2007/0259957 A1 | 11/2007 | Ueshima et al. |
| 2009/0030077 A1 | 1/2009 | Almarsson et al. |

FOREIGN PATENT DOCUMENTS

| | | |
|---|---|---|
| JP | 10-287563 A | 10/1998 |
| JP | 2001-525363 A | 12/2001 |
| JP | 2002-513750 A | 5/2002 |
| JP | 2008-516890 A | 5/2008 |
| JP | 2008-178341 A | 8/2008 |
| JP | 2008/533029 A | 8/2008 |
| WO | WO 99/56727 A2 | 11/1999 |
| WO | WO 2005/065652 A1 | 7/2005 |
| WO | WO 2006/096806 A2 | 9/2006 |

OTHER PUBLICATIONS

Extended European Search Report, dated May 4, 2017, for European Application No. 17000014.5.
Committee for Veterinary Medicinal Products, Polyoxyl Castor Oil, Polyoxyl Hydrogenated Castor Oil, Summary Report, The European Agency for the Evaluation of Medicinal Products, Veterinary Medicines Evaluation unit, Jun. 1999 (1 page).
Communication Pursuant to Article 94(3) EPC dated Oct. 13, 2014, in European Patent Application No. 10777845.8.
International Preliminary Report on Patentability dated May 21, 2010, in PCT International Application No. PCT/JP2010/058676.
International Search Report for PCT/JP2010/058676, dated Jun. 22, 2010.
P. Ratanabanangkoon et al.,"A high-throughput approach towards a novel formulation of fenofibrate in omega-3 oil", European Journal of Pharmaceutical Sciences, vol. 33, 2008, pp. 351-360.
Japanese Office Action and a partial English translation, dated May 31, 2016, for Japanese Application No. 2016-061805.

*Primary Examiner* — Savitha M Rao
(74) *Attorney, Agent, or Firm* — Birch, Stewart, Kolasch & Birch, LLP

(57) ABSTRACT

This invention provides a self-emulsifying composition comprising 50 to 95% by weight in total of at least one compound selected from the group consisting of ω3 polyunsaturated fatty acids and their pharmaceutically acceptable salts and esters; and 5 to 50% by weight of an emulsifier having a hydrophilic lipophilic balance of at least 10. The composition has no or reduced ethanol content, and exhibits excellent self-emulsifying property, dispersibility in the composition, emulsion stability, and absorption property. The composition is adapted for use as a drug.

13 Claims, No Drawings

SELF-EMULSIFYING COMPOSITION OF ω3 FATTY ACID

CROSS-REFERENCE TO RELATED APPLICATIONS

This application is a 37 C.F.R. § 1.53(b) continuation of U.S. application Ser. No. 14/745,888, filed Jun. 22, 2015, which is a divisional of U.S. application Ser. No. 14/069,718, filed Nov. 1, 2013, (now U.S. Pat. No. 9,089,483 B2), which is a divisional of U.S. application Ser. No. 13/321,801, filed Nov. 21, 2011, (now U.S. Pat. No. 8,618,168 B2), which is the National Phase of PCT International Application No. PCT/JP2010/058676 filed May 21, 2010, which claims priority on Japanese Patent Application No. 2009-124444 filed May 22, 2009. The entire contents of each application are hereby incorporated by reference.

TECHNICAL FIELD

This invention provides a self-emulsifying composition containing at least one compound selected from the group consisting of ω3 polyunsaturated fatty acids and their pharmaceutically acceptable salts and esters thereof. This invention also provides a drug of such self-emulsifying composition, its production method, and a method for its use.

BACKGROUND ART

Known ω3 polyunsaturated fatty acids (hereinafter abbreviated as ω3PUFA) include α-linolenic acid, eicosapentaenoic acid (hereinafter abbreviated as EPA), and docosahexaenoic acid (hereinafter abbreviated as DHA). Since ω3PUFA and pharmaceutically acceptable salts and esters thereof have various actions such as anti-arteriosclerosis action, platelet aggregation suppressive action, blood lipid lowering action, anti-inflammatory action, carcinostatic action, and central action, they are blended in various food products, and commercially sold in the form of health food and medical and pharmaceutical products.

Ethyl eicosapentaenoate ester (hereinafter abbreviated as EPA-E) is commercially sold as an oral therapeutic agent for ameliorating ulcer, pain, and coldness associated with arteriosclerosis obliterans as well as hyperlipidemia (product name Epadel, Mochida Pharmaceutical Co., Ltd.). When EPA-E is administered orally under fasting, increase in plasma EPA concentration is smaller than the case of the oral administration after the meal conceivably because absorption of the EPA-E requires secretion of bile acid and food components as a carrier. Accordingly, Epadel is instructed to be orally administered three times a day each time immediately after the meal (see Non-Patent Literature 1).

However, dosage method or drug compliance has become a problem for those people not taking meals three times a day with the recent change in the life style, patients who can only take meals at a reduced amount, patients who can only take a fluid diet (milk, rice broth, starch gruel, egg, soup, juice, or oral nutritional supplement), patients with reduced absorption ability of the intestinal tract (for example, elderly, patients of intestinal disease, patients after intestinal surgery, terminal cancer patients, and patients taking a lipase inhibitor), or patients who are unable to take meals such as those after the cerebral infarction.

Recently, attention is paid to the relation between non-fasting hypertriglyceridemia, namely the condition in which serum triglyceride (hereinafter abbreviated as TG) is at its normal value under fasting while abnormally increased serum TG value is observed after taking meal or for a prolonged period after taking the meal and coronary artery disease (see Non-Patent Literature 2), and one cause which may be associated with this relation is enhancement of sterol regulatory element binding protein 1c (hereinafter abbreviated as SREBP1c). Prevention and improvement of lipotoxicity of pancreas β cell under the load of palmitic acid by continuous oral administration of the EPA-E under feeding has been reported, and involvement of the suppression of the SREBP1c in the mechanism has also been reported (see Non-Patent Literature 3). However, there is no report for the effectiveness of oral administration before the meal (under fasting), and an ω3PUFA preparation which is rapidly absorbed even if administered before the meal to suppresses increase of postprandial serum TG is highly awaited.

An emulsion composition containing an ω3PUFA, its pharmaceutically acceptable salt or ester exhibiting good processing and storage stability, which is gradually absorbed by oral administration and which exhibits prolonged absorption for a prolonged period has been reported (see Patent Literature 1). This composition comprises EPA-E and an emulsifier such as a polyglycerin fatty acid ester having a triglycerin content in polyglycerin of at least 60% or polyoxyethylene sorbitan fatty acid ester.

However, in the case of an emulsion preparation, content of the ω3PUFA, its pharmaceutically acceptable salt or ester which is the effective component is at most not more than several dozen percents, and moisture content is high. Accordingly, the entire amount of the preparation and the moisture that should be taken for the intake of a pharmaceutically effective amount is inevitably high, and administration of such amount is difficult for the patients such as dialysis patients whose water intake is limited, and the high water content means difficulty of capsulation in a capsule which is made of a material like gelatin. The high moisture content also results in the increase in the handling trouble and cost in the production, distribution, and storage.

A self-emulsifying preparation which does not contain water in the preparation and which is readily dispersible and self-emulsifying in water has been reported (see Patent Literature 2 and Non-Patent Literature 4). This preparation contains ω3PUFA and fenofibrate as its effective components, ethanol, and a surfactant.

Because of the inclusion of the ethanol in the composition, this composition is believed to suffer from the problems such as volatilization of the ethanol in the course of capsulation, and in particular, in the step of drying which invites increase in the risk of capsule deformation and bubble entrapment, volatilization of the ethanol in the course of distribution and storage which invites increase in the risk of capsule deformation and cracks, and denaturing and turbidity of the capsule content caused by the change in the composition due to the volatilization of the ethanol. Furthermore, such preparation including the ethanol can not be taken or such intake is difficult for the alcohol (ethanol) intolerant patients who suffer from face and systemic blush, increase in the heart and respiratory rates, as well as headache and vomiting by the small amount of alcohol intake due to the lack of aldehyde dehydrogenase which is an alcohol decomposition enzyme or the insufficient activity of the dehydrogenase. Such people genetically lacking the alcohol decomposition enzyme or those having low activity dehydrogenase are found in Mongoloids including Japanese at a high rate, and more specifically, in 40 to 45% of Japanese population, and in such a case, high ethanol content in the preparation should result in various disorders as apparent to those skilled in the art. For example, "Dictionary of Drug Additives (in Japanese)" discloses the maximum daily ethanol dose of 3.26 mg in the case of oral administration (see Non-Patent Literature 5).

In addition, there has so far been no report of the preparation which is less affected by meals and which can be administered to a patient who is unable to take meals or which can be orally administered to a patient under fasting such as a patient before going to bed; a preparation which can rapidly increase blood ω3PUFA concentration by the administration under fasting such as administration before the meal or before going to bed and which can rapidly and effectively realize the intended pharmacological action, for example, suppression of the increase of the postprandial serum TG; an ω3PUFA preparation which can be encapsulated in a gelatin capsule or the like and which can be used at a reduced volume; or a preparation with no or reduced ethanol content that have solved the ethanol-related problems as described above.

CITATION LIST

Patent Literature

Patent Literature 1: JP 2008-178341 A
Patent Literature 2: JP 2008-516890 A

Non-Patent Literature

Non-Patent Literature 1: Epadel S (Drug Interview Form), Mochida Pharmaceutical Co., Ltd., March, 2007
Non-Patent Literature 2: "Guideline for Diagnosis and Prevention of Atherosclerotic Cardiovascular Diseases, 2007 Edition" edited by Japan Atherosclerosis Society and published by Kyowa Kikaku Ltd., Apr. 25, 2007
Non-Patent Literature 3: Diabetes, vol. 57, no. 9, 2382-2392, 2008
Non-Patent Literature 4: European Journal of Pharmaceutical Sciences, vol. 33, 351-360, 2008
Non-Patent Literature 5: "2007 Dictionary of Drug Additives" edited by International Pharmaceutical Excipients Council Japan and published by Yakuji Nippo Ltd., Jul. 25, 2007)

SUMMARY OF INVENTION

Technical Problems

An object of the present invention is to provide a self-emulsifying composition which contains at least one compound selected from the group consisting of ω3PUFA, its pharmaceutically acceptable salts and esters and an emulsifier having a hydrophilic lipophilic balance (hereinafter abbreviated as HLB) of at least 10, which has at least one of excellent self-emulsifying property, dispersibility in the composition, emulsion stability, and absorption property, which contains no ethanol or has a low ethanol concentration, and which is capable of obviating the problems caused by the ethanol inclusion. The present invention also provides a drug of such self-emulsifying composition, its production method, and the method of its use.

Solution to Problems

In order to solve the problems as described above, the inventors of the present invention reduced ethanol content (15% by weight) of the self-emulsifying composition described in Table 4 of Non-Patent Literature 4, and thereby found that the composition was cloudy and not fully miscible when the ethanol content was reduced to 10% by weight or less. Next, the ethanol was partly substituted with propylene glycol which is a polyhydric alcohol, and the composition also became cloudy and not fully miscible when the ethanol content was reduced to 11% by weight or less, and the problems were not solved.

In conducting further intensive investigation, the inventors found that a composition containing at least one compound selected from the group consisting of ω3PUFAs and their pharmaceutically acceptable salts and esters at a total content of 50 to 95% by weight and an emulsifier having an HLB of at least 10, for example, an emulsifier which is at least one member selected from polyoxyethylene hydrogenated castor oil, polyoxyethylene sorbitan fatty acid ester, polyoxyethylene castor oil, polyethylene glycol fatty acid ester, polyoxyethylene polyoxypropylene glycol, sucrose fatty acid ester, and lecithin at a total content of 5 to 50% by weight would be a self-emulsifying composition exhibiting at least one of excellent self-emulsifying property, dispersibility in the composition, emulsion stability, and absorption property, and in particular, oral absorption property and rate under fasting even if no ethanol was added or the ethanol was added at a low concentration. The present invention has been completed on the basis of such finding. The embodiments of the present invention as described below.

(1) A self-emulsifying composition comprising 50 to 95% by weight in total of at least one compound selected from the group consisting of ω3PUFA and pharmaceutically acceptable salts and esters thereof; and 5 to 50% by weight of an emulsifier having a hydrophilic lipophilic balance of at least 10; wherein ethanol content is up to 4% by weight in relation to the total content of the compound and the emulsifier.

(2) A self-emulsifying composition according to the above (1) wherein content of the ethanol is up to 1% by weight.

(3) A self-emulsifying composition according to the above (1) or (2) wherein the composition does not contain ethanol.

(4) A self-emulsifying composition according to any one of the above (1) to (3) wherein the emulsifier is at least one member selected from the group consisting of polyoxyethylene hydrogenated castor oil, polyoxyethylene sorbitan fatty acid ester, polyoxyethylene castor oil, polyethylene glycol fatty acid ester, polyoxyethylene polyoxypropylene glycol, sucrose fatty acid ester, and lecithin.

(5) A self-emulsifying composition according to any one of the above (1) to (4) wherein the emulsifier is at least one member selected from the group consisting of polyoxyethylene hydrogenated castor oil, polyoxyethylene sorbitan fatty acid ester, polyoxyethylene castor oil, and sucrose fatty acid ester.

(6) A self-emulsifying composition according to any one of the above (1) to (5) wherein the polyoxyethylene hydrogenated castor oil is at least one member selected from the group consisting of polyoxyethylene (20) hydrogenated castor oil, polyoxyethylene (40) hydrogenated castor oil, polyoxyethylene (50) hydrogenated castor oil, polyoxyethylene (60) hydrogenated castor oil, and polyoxyethylene (100) hydrogenated castor oil.

(7) A self-emulsifying composition according to any one of the above (1) to (5) wherein the polyoxyethylene sorbitan fatty acid ester is at least one member selected from the group consisting of polyoxyethylene sorbitan monooleate, polyoxyethylene sorbitan tristearate, polyoxyethylene sorbitan monostearate, polyoxyethylene sorbitan monopalmitate, and polyoxyethylene sorbitan monolaurate.

(8) A self-emulsifying composition according to any one of the above (1) to (5) wherein the sucrose fatty acid ester is at least one member selected from the group consisting of sucrose laurate, sucrose myristate, sucrose palmitate, sucrose stearate, and sucrose oleate.

(9) A self-emulsifying composition according to any one of the above (1) to (8) wherein the composition contains a lecithin.

(10) A self-emulsifying composition according to the above (9) wherein the lecithin is at least one member selected from the group consisting of soybean lecithin, enzymatically decomposed soybean lecithin, hydrogenated soybean lecithin, and egg yolk lecithin.

(11) A self-emulsifying composition according to any one of the above (1) to (8) wherein the composition contains a polyhydric alcohol.

(12) A self-emulsifying composition according to the above (11) wherein the polyhydric alcohol is at least one member selected from the group consisting of divalent alcohols such as ethylene glycol, propylene glycol, trimethylene glycol, 1,2-butylene glycol, tetramethylene glycol, 1,3-butylene glycol, 2,3-butylene glycol, and pentamethylene glycol; trivalent alcohols such as glycerin, trimethylolpropane, and 1,2,6-hexanetriol; and polyhydric alcohol polymers such as diethylene glycol, dipropylene glycol, triethylene glycol, polyethylene glycol, polypropylene glycol, and polyglycerin.

(13) A self-emulsifying composition according to the above (11) wherein the polyhydric alcohol is propylene glycol or glycerin.

(14) A self-emulsifying composition according to any one of the above (1) to (13) wherein the composition contains lecithin and a polyhydric alcohol.

(15) A self-emulsifying composition according to any one of the above (1) to (14) wherein the emulsifier is at least one member selected from the group consisting of polyoxyethylene hydrogenated castor oil, polyoxyethylene sorbitan fatty acid ester, and polyoxyethylene castor oil, and the polyhydric alcohol is propylene glycol.

(16) A self-emulsifying composition according to any one of the above (1) to (14) wherein the emulsifier is a sucrose fatty acid ester and the polyhydric alcohol is glycerin.

(17) A self-emulsifying composition according to any one of the above (1) to (16) wherein content of the at least one compound selected from the group consisting of ω3PUFA and its pharmaceutically acceptable salts and esters is in the range of 55 to 90% by weight.

(18) A self-emulsifying composition according to any one of the above (1) to (17) wherein content of the at least one compound selected from the group consisting of ω3PUFA and its pharmaceutically acceptable salts and esters is in the range of 60 to 80% by weight.

(19) A self-emulsifying composition according to any one of the above (1) to (18) wherein content of the at least one compound selected from the group consisting of ω3PUFA and its pharmaceutically acceptable salts and esters is in the range of 65 to 75% by weight.

(20) A self-emulsifying composition according to any one of the above (1) to (19) wherein total content of the emulsifier having an HLB of at least 10 is 10 to 100 parts by weight in relation to 100 parts by weight of the at least one compound selected from the group consisting of ω3 PUFA and pharmaceutically acceptable salts and esters thereof.

(21) A self-emulsifying composition according to any one of the above (1) to (20) wherein total content of the emulsifier having an HLB of at least 10 is 10 to 80 parts by weight in relation to 100 parts by weight of the at least one compound selected from the group consisting of ω3 PUFA and pharmaceutically acceptable salts and esters thereof.

(22) A self-emulsifying composition according to any one of the above (1) to (21) wherein total content of the emulsifier having an HLB of at least 10 is 10 to 50 parts by weight in relation to 100 parts by weight of the at least one compound selected from the group consisting of ω3 PUFA and pharmaceutically acceptable salts and esters thereof.

(23) A self-emulsifying composition according to any one of the above (1) to (22) wherein, when the self-emulsifying composition is orally administered to a male beagle which has been fasted for at least 18 hours at an amount corresponding to 600 mg of the at least one compound selected from the group consisting of ω3PUFA and pharmaceutically acceptable salts and esters thereof, maximum blood ω3PUFA concentration (corrected by subtracting the blood ω3 concentration before the administration of the composition) is at least 50 µg/ml, and/or area under the blood ω3PUFA concentration vs time curve from the administration to two hours after the administration is at least 50 µg/ml hr.

(24) A self-emulsifying composition according to any one of the above (1) to (22) wherein, when the self-emulsifying composition is orally administered to a male beagle which has been fasted for at least 18 hours at an amount corresponding to 600 mg of the at least one compound selected from the group consisting of ω3PUFA and pharmaceutically acceptable salts and esters thereof, maximum blood ω3PUFA concentration (corrected by subtracting the blood ω3 concentration before the administration of the composition) is at least 60 µg/ml, and/or area under the blood ω3PUFA concentration vs time curve from the administration to two hours after the administration is at least 60 µg/ml hr.

(25) A self-emulsifying composition according to any one of the above (1) to (22) wherein, when the self-emulsifying composition is orally administered to a male beagle which has been fasted for at least 18 hours at an amount corresponding to 600 mg of the at least one compound selected from the group consisting of ω3PUFA and pharmaceutically acceptable salts and esters thereof, maximum blood ω3PUFA concentration (corrected by subtracting the blood ω3 concentration before the administration of the composition) is at least 70 µg/ml, and/or area under the blood ω3PUFA concentration vs time curve from the administration to two hours after the administration is at least 70 µg/ml hr.

(26) A self-emulsifying composition according to any one of the above (1) to (22) wherein, when the self-emulsifying composition is orally administered to a male cynomolgus monkey which has been fasted for at least 12 hours at an amount corresponding to 45 mg per kg body weight of the at least one compound selected from the group consisting of ω3PUFA and pharmaceutically acceptable salts and esters thereof, maximum blood ω3PUFA concentration (corrected by subtracting the blood ω3 concentration before the administration of the composition) is at least 50 µg/ml, and/or area under the blood ω3PUFA concentration vs time curve from the administration to twelve hours after the administration is at least 400 µg/ml hr.

(27) A self-emulsifying composition according to any one of the above (1) to (22) wherein, when the self-emulsifying composition is orally administered to a male cynomolgus monkey which has been fasted for at least 12 hours at an amount corresponding to 45 mg per kg body weight of the at least one compound selected from the group consisting of ω3PUFA and pharmaceutically acceptable salts and esters thereof, maximum blood ω3PUFA concentration (corrected by subtracting the blood ω3 concentration before the administration of the composition) is at least 70 µg/ml, and/or area under the blood ω3PUFA concentration vs time curve from the administration to twelve hours after the administration is at least 500 µg/ml hr.

(28) A self-emulsifying composition according to any one of the above (1) to (22) wherein, when the self-emulsifying composition is orally administered to human at an amount corresponding to 1800 mg of the at least one compound selected from the group consisting of ω3PUFA and pharmaceutically acceptable salts and esters thereof, maximum blood ω3PUFA concentration (corrected by subtracting the blood ω3 concentration before the administration of the composition) is at least 50 µg/ml, and/or blood ω3PUFA concentration at 2 hours after the administration is at least 10 µg/ml.

(29) A self-emulsifying composition according to any one of the above (1) to (28) containing at least one member selected from the group consisting of EPA, DHA, their pharmaceutically acceptable salts and esters as its effective component.

(30) A self-emulsifying composition according to any one of the above (1) to (29) containing EPA-E and/or ethyl ester of DHA as its effective component.

(31) A self-emulsifying composition according to any one of the above (1) to (30) containing EPA-E as its effective component.

(32) A self-emulsifying composition according to any one of the above (1) to (31) further comprising at least one member selected from the group consisting of polyenephosphatidylcholine, unsaponifiable soybean oil (soy sterol), gamma-oryzanol, riboflavin butyrate, dextran sulfate sodium sulfur 18, pantethine, elastase, pravastatin, simvastatin, atorvastatin, fluvastatin, pitavastatin, rosuvastatin, cerivastatin, simfibrate, clofibrate, clinofibrate, bezafibrate, fenofibrate, orlistat, cetilistat, colestyramine, colestimide, ezetimibe, vitamin C, vitamin E, tocopherol nicotinate, N-acetylcysteine, probucol, irbesartan, olmesartan medoxomil, candesartan cilexetil, telmisartan, valsartan, losartan potassium, alacepril, imidapril hydrochloride, enalapril maleate, captopril, quinapril hydrochloride, cilazapril hydrate, temocapril hydrochloride, delapril hydrochloride, trandolapril, benazepril hydrochloride, perindopril, lisinopril hydrate, azelnidipine, amlodipine besylate, aranidipine, efonidipine hydrochloride, cilnidipine, nicardipine hydrochloride, nifedipine, nimodipine, nitrendipine, nilvadipine, barnidipine hydrochloride, felodipine, benidipine, manidipine, tolazoline, phentolamine, atenolol, metoprolol, acebutolol, propranolol, pindolol, carvedilol, labetalol hydrochloride, clonidine, methyldopa, eplerenone, hydrochlorothiazide, furosemide, acarbose, voglibose, miglitol, gliclazide, glibenclamide, glimepiride, tolbutamide, nateglinide, mitiglinide, metformin hydrochloride, buformin hydrochloride, sitagliptin, vildagliptin, alogliptin, saxagliptin, pioglitazone hydrochloride, rosiglitazone maleate, exenatide, liraglutide cilostazol, ticlopidine hydrochloride, alprostadil, limaprost, beraprost sodium, sarpogrelate hydrochloride, argatroban, naftidrofuryl, isoxsuprine hydrochloride, batroxobin, dihydroergotoxine mesilate, tolazoline hydrochloride, hepronicate, shimotsu-to extract, ursodeoxycholic acid, chenodeoxycholic acid, bile powder, deoxycholic acid, cholic acid, bile extract, bear bile, oriental bezoar, dehydrocholic acid, biotin, cyanocobalamin, pantothenic acid, folic acid, thiamine, vitamin K, tyrosine, pyridoxine, leucine, isoleucine, valine, calcium, iron, zinc, copper, magnesium, soy protein, chitosan, low molecular weight sodium alginate, dietary fiber from psyllium seed coat, soy peptide with bound phospholipids, phytosterol ester, plant stanol ester, diacylglycerol, globin digest, and tea catechin as its second effective component.

(33) A self-emulsifying composition according to any one of the above (1) to (32) wherein the moisture content is up to 10% by weight.

(34) A drug which is a self-emulsifying composition comprising 50 to 95% by weight in total of at least one compound selected from the group consisting of ω3PUFA and pharmaceutically acceptable salts and esters thereof; and 5 to 50% by weight of an emulsifier having a hydrophilic lipophilic balance of at least 10; wherein ethanol content is up to 4% by weight in relation to the total content of the compound and the emulsifier.

(35) A drug according to the above (34) wherein content of the ethanol is up to 1% by weight.

(36) A drug according to the above (34) or (35) which does not contain ethanol.

(37) A drug which is a self-emulsifying composition of any one of the above (1) to (33).

(38) A drug according any one of the above (34) to (37) wherein the drug is at least one member selected from the group consisting of therapeutic agent for dyslipidemia, therapeutic agent for postprandial hypertriglyceridemia, anti-arteriosclerosis agent, platelet aggregation suppressant, therapeutic agent for peripheral circulatory insufficiency, therapeutic agent for inflammatory disease, anticancer agent, and therapeutic agent for central disease.

(39) A method for producing the self-emulsifying composition of any one of the above (1) to (33) comprising the steps of mixing at least 10 parts by weight the emulsifier having an HLB of at least 10 in relation to 100 parts by weight in total of the at least one compound selected from the group consisting of ω3PUFA and pharmaceutically acceptable salts and esters thereof, and homogenizing the mixture (with the proviso that the homogenization is production of a homogeneous composition of the ω3PUFA and the emulsifier by dissolution or dispersion which is accomplished by a step such as heating or stirring).

(40) A method for administering human under fasting or before sleeping with at least one compound selected from the group consisting of ω3PUFA and pharmaceutically acceptable salts and esters thereof, comprising the steps of adding at least 10 parts by weight the emulsifier having an HLB of at least 10 to 100 parts by weight in total of the compound, stirring the mixture, and administering the mixture to human.

(41) A method for increasing plasma ω3PUFA concentration comprising the steps of adding at least 10 parts by weight the emulsifier having an HLB of at least 10 to 100 parts by weight in total of at least one compound selected from the group consisting of ω3PUFA and pharmaceutically acceptable salts and esters thereof, stirring the mixture, and administering the mixture to human under fasting or before sleeping to thereby increase the plasma ω3PUFA concentration.

Advantageous Effects of Invention

By adding and dissolving an emulsifier having an HLB of at least 10 to at least one compound selected from the group consisting of ω3PUFA, its pharmaceutically acceptable salts and esters, the present invention is capable of providing a self-emulsifying composition which has at least one of excellent self-emulsifying property, dispersibility in the composition, emulsion stability, and absorption property, and in particular, oral absorption property and rate under fasting, and which contains no ethanol or has a low ethanol concentration, and which is capable of obviating the problems caused by the ethanol inclusion. The present invention also provides a drug of such self-emulsifying composition, its production method, and the method of its use.

Compared to conventional compositions, the self-emulsifying composition of the present invention which can be rapidly absorbed even in the case of oral administration under fasting is expected to show preventive, ameliorating, and therapeutic effects of the ω3PUFA for various diseases. More specifically, the self-emulsifying composition of the present invention shows its effectiveness by the administration of 1 to 3 times a day at non-limited timing, namely, without the limitation of the administering three times a day immediately after the meal, and this convenience for the patients leads to the improved drug compliance, and hence, further improvement in the effectiveness. In addition, the self-emulsifying composition of the present invention can be combined with a drug which is administered not by the administration immediately after the meal, and a drug which is a combination with such drug may also be produced. Furthermore, the self-emulsifying composition of the present invention is expected to show various clinical merits such as suppression of the serum TG increase after the meal by administering the composition before the meal and prevention of essential fatty acid deficiency associated with lipase inhibitor administration by administration of the composition before going to the bed.

Compared to the conventional emulsion preparation, the self-emulsifying composition of the present invention can be produced, delivered, and stored at reduced cost and with less trouble. In addition, the self-emulsifying composition of the present invention can be prepared water-free with higher concentration of the effective components, and hence, at reduced preparation volume, and this enables administration of the composition to patients with water intake restriction. Furthermore, the self-emulsifying composition of the present invention can be encapsulated in a gelatin capsule or the like, and this is expected to improve both drug convenience and drug compliance.

Due to the non-inclusion or reduced inclusion of the ethanol in the self-emulsifying composition of the present invention, this composition has reduced risk of capsule deformation and bubble entrapment by the ethanol volatilization during the capsulation step, and in particular, during the drying step, and also, reduced risk of quality change such as capsule deformation and crack generation by the ethanol volatilization during the distribution and storage process. This composition also has reduced risk of the denaturing such as clouding and separation of the capsule content by the ethanol volatilization. Furthermore, side effects of the ethanol are absent or reduced in alcohol (ethanol) intolerant patients, and it is expected that the composition can be safely administered for a long period.

Of the ω3PUFAs and pharmaceutically acceptable salts and esters thereof, EPA-E is known as a highly safe drug effective component. However, on rare occasion, EPA-E suffers from side effects such as vomiturition (0.21%), nausea (0.23%), and stomach discomfort (0.23%). The present invention is expected to enable decrease of the dose and/or frequency of the at least one compound selected from the group consisting of ω3PUFA and pharmaceutically acceptable salts and esters thereof, and the amelioration of the side effects leads to improvement in the drug compliance, and also, continuation of the therapy in the patients who would have been forced to terminate the administration due to the side effects.

In addition, an ameliorating or therapeutic drug for chronic diseases such as dyslipidemia basically needs continuous administration for a long period, and in the case of such administration, the present invention is expected to realize amelioration and treatment by reduced dose and frequency.

In advanced countries such as Japan, the U.S., and Europe, use of alternative medicine has increased, and examples include use of special purpose foods, functional health foods (designated health food and functional nutritional food), and health foods (supplements). The self-emulsifying composition containing at least one compound selected from the group consisting of ω3PUFA and pharmaceutically acceptable salts and esters thereof and an emulsifier having an HLB of at least 10 can be provided as a functional health food for human for those in need of the ω3PUFA, for example, those suffering from or those within the risk of suffering from dyslipidemia, peripheral circulatory insufficiency, and metabolic syndrome in order to prevent further occurrence of the cerebrovascular event or progress into ulcer and gangrene of extremities and peripheries to thereby maintain the quality of life.

DESCRIPTION OF EMBODIMENTS

Next, the present invention is described in detail.

The present invention is a self-emulsifying composition comprising 50 to 95% by weight in total of at least one compound selected from the group consisting of ω3 PFUA and pharmaceutically acceptable salts and esters thereof; and 5 to 50% by weight of an emulsifier having an HLB of at least 10. The self-emulsifying composition is free from ethanol or the ethanol content is low. The present invention also provides a drug of such self-emulsifying composition, its production method, and the method of its use.

In the present invention, "ω3PUFA" is a fatty acid having a plurality of carbon-carbon double bonds in the molecule, and the first double bond is at 3rd position from the end on the side of the methyl group. Typical examples include α-linolenic acid, EPA, DHA, eicosatrienoic acid, stearidonic acid, eicosatetraenoic acid, clupanodonic acid, tetracosapentaenoic acid, and nisinic acid. In the present invention, the term "ω3PUFA" include not only the ω3PUFA but also their pharmaceutically acceptable salts and esters unless otherwise noted.

The ω3PUFA used in the present invention may be a synthetic, semi-synthetic, natural ω3PUFA, or a natural oil containing such ω3PUFA. Examples of the natural ω3PUFA include an extract from a natural oil containing an ω3PUFA, a crudely purified natural oil containing an ω3PUFA, and a highly purified natural oil containing an ω3PUFA produced by a method known in the art. Exemplary semi-synthetic ω3PUFAs include ω3PUFAs produced by a microorganism or the like and the ω3PUFAs or the natural ω3PUFAs which have been subjected to a chemical treatment such as esterification or ester exchange. In the present invention, any one of the ω3PUFAs may be used alone or in combination of two or more.

In the present invention, EPA and DHA are the preferable examples of the ω3PUFAs, and EPA is more preferable. Examples of the pharmaceutically acceptable salts of the ω3PUFA include inorganic salts such as sodium salts and potassium salts, organic salts such as benzylamine salts and diethylamine salts, salts with basic amino acids such as arginine salts and lysine salts, and exemplary esters include alkyl esters such as ethyl ester, and esters such as mono-, di-and TG. Preferable examples include ethyl ester and TG ester, and the more preferred is ethyl ester. More specifically, preferable examples include EPA-E, TG ester of EPA, ethyl DHA ester (hereinafter abbreviated as DHA-E), and TG ester of DHA, and among these, the more preferred are EPA-E and DHA-E, and the most preferred is EPA-E.

The ω3PUFA used for the starting material of the self-emulsifying composition of the present invention is not particularly limited for its purity. The purity is typically such that content of the ω3PUFA in the composition of the present invention could be preferably at least 50% by weight, more preferably at least 70% by weight, still more preferably at least 80% by weight, still more preferably at least 90% by weight, and most preferably at least 96.5% by weight. The ω3PUFA containing EPA-E and DHA-E at a high purity, for example, the one with the content of (EPA-E+DHA-E) in relation to the ω3PUFA of at least 50% by weight is preferable, and the content is more preferably at least 60% by weight, still more preferably at least 90% by weight, and most preferably at least 98% by weight. In other words, the composition of the present invention preferably has a high purity of ω3PUFAs in the total fatty acid, more preferably, a high purity of (EPA+DHA) which are ω3PUFAs, and still more preferably, a high purity of EPA.

For example, when EPA-E and DHA-E are used, compositional ratio of EPA-E/DHA-E and content of (EPA-E+DHA-E) in relation to total fatty acid are not particularly limited as long as the purity of EPA in the composition of the present invention is in the range as described above. However, the compositional ratio of the EPA-E/DHA-E is preferably at least 0.8, more preferably at least 1.0, and most preferably at least 1.2.

The composition of the present invention may also contain a polyunsaturated fatty acid other than the ω3PUFA such as linoleic acid, γ linolenic acid, or dihomo-γ-linolenic acid or the pharmaceutically acceptable salt or ester thereof. However, content of arachidonic acid is preferably low, more preferably less than 2% by weight, still more preferably less than 1% by weight, and most preferably, the composition is substantially free from the arachidonic acid.

In the self-emulsifying composition of the present invention, content of the ω3PUFA is 50 to 95% by weight, preferably 55 to 90% by weight, more preferably 60 to 80% by weight, and still more preferably 65 to 75% by weight.

Compared to the fish oil or the fish oil concentrate, the ω3PUFA used in the composition or therapeutic agent of the present invention contains impurities such as saturated fatty acids and arachidonic acid which are unfavorable for cardiovascular events at a lower content, and this enables realization of the intended action without causing the problems of excessive nutrition or vitamin A intake. When the ω3PUFA in the form of ester is used, a sufficiently stable composition can be obtained by adding a commonly used antioxidant since the ester form has higher oxidation stability than the fish oils which are mainly TG form.

The ω3PUFA used may be a soft capsule containing the EPA-E at a high purity (at least 96.5% by weight) (product name, Epadel; manufactured by Mochida Pharmaceutical Co., Ltd.) available in Japan as a therapeutic agent for ASO and hyperlipidemia. The ω3PUFA used may also be a mixture of EPA-E and DHA-E, for example, Lovaza (Registered Tradename) from GlaxoSmithKline which is a soft capsule containing about 46.5% by weight of EPA-E and about 37.5% by weight of DHA-E) commercially available in the U.S. as a therapeutic agent for hypertriglyceridemia.

Purified fish oils may also be used for the ω3PUFA, and use of monoglyceride, diglyceride, and TG derivatives and combinations thereof of the ω3PUFA are also preferable embodiments. Various products containing the ω3PUFA are commercially available, for example, Incromega F2250, F2628, E2251, F2573, TG2162, TG2779, TG2928, TG3525, and E5015 (Croda International PLC, Yorkshire, England), and EPAX6000FA, EPAX5000TG, EPAX4510TG, EPAX2050TG, EPAX7010EE, K85TG, K85EE, and K80EE (Pronova Biopharma, Lysaker, Norway). These products may be purchased and used for the composition of the present invention.

In the present invention, the "polyoxyethylene hydrogenated castor oil" is a compound prepared by addition polymerization of ethylene oxide to the hydrogenated castor oil which is castor oil having hydrogen added thereto. Various compounds with different average degree of polymerization of ethylene oxide are commercially available, and examples include polyoxyethylene (20) hydrogenated castor oil (NIKKOL HCO-20, Nikko Chemicals Co., Ltd.), polyoxyethylene (40) hydrogenated castor oil (NIKKOL HCO-40, Nikko Chemicals Co., Ltd.), polyoxyethylene (50) hydrogenated castor oil (NIKKOL HCO-50, Nikko Chemicals Co., Ltd.), polyoxyethylene (60) hydrogenated castor oil (NIKKOL HCO-60, Nikko Chemicals Co., Ltd.), and polyoxyethylene (100) hydrogenated castor oil (NIKKOL HCO-100, Nikko Chemicals Co., Ltd.), and the preferred is polyoxyethylene (60) hydrogenated castor oil. These may be used alone or in combination of two or more. In the present invention, the "polyoxyethylene hydrogenated castor oil" includes all of such compounds unless otherwise noted.

In the present invention, the "polyoxyethylene sorbitan fatty acid ester" is polyoxyethylene ether of a fatty acid ester wherein a part of the hydroxy groups of anhydrous sorbitol have been esterified with a fatty acid. Various compounds with different esterified fatty acid are commercially available, and examples include polyoxyethylene (20) sorbitan monolaurate (NIKKOL TL-10, Nikko Chemicals Co., Ltd.), polyoxyethylene (20) sorbitan monopalmitate (NIKKOL TP-10V, Nikko Chemicals Co., Ltd.), polyoxyethylene (20) sorbitan monostearate (NIKKOL TS-10V, Nikko Chemicals Co., Ltd.), polyoxyethylene (20) sorbitan tristearate (NIKKOL TS-30V, Nikko Chemicals Co., Ltd.), polyoxyethylene (20) sorbitan monoisostearate (NIKKOL TI-10V, Nikko Chemicals Co., Ltd.), polyoxyethylene (20) sorbitan monooleate (NIKKOL TO-10V, Nikko Chemicals Co., Ltd.), and polyoxyethylene (20) sorbitan trioleate (NIKKOL TO-30V, Nikko Chemicals Co., Ltd.), and the preferred are polyoxyethylene (20) sorbitan monolaurate, polyoxyethylene (20) sorbitan monopalmitate, polyoxyethylene (20) sorbitan monostearate, and polyoxyethylene (20) sorbitan monooleate, and the more preferred are polyoxyethylene (20) sorbitan monooleate. These may be used alone or in combination of two or more. In the present invention, the "polyoxyethylene sorbitan fatty acid ester" includes all of such compounds unless otherwise noted.

In the present invention, the "polyoxyethylene castor oil" is a compound prepared by addition polymerization of ethylene oxide to castor oil. Various compounds having different average ethylene oxide mole number are commercially available, and examples include NIKKOL CO-3 with an average ethylene oxide mole number of 3 (Nikko Chemicals Co., Ltd.), NIKKOL CO-10 with an average ethylene oxide mole number of 10 (Nikko Chemicals Co., Ltd.), EMALEX C-20 with an average ethylene oxide mole number of 20 (Nippon Emulsion Co., Ltd.), EMALEX C-30 with an average ethylene oxide mole number of 30 (Nippon Emulsion Co., Ltd.), EMALEX C-40 with an average ethylene oxide mole number of 40 (Nippon Emulsion Co., Ltd.), and EMALEX C-50 with an average ethylene oxide mole number of 50 (Nippon Emulsion Co., Ltd.). These may be used alone or in combination of two or more. In the present invention, the "polyoxyethylene castor oil" includes all of such compounds unless otherwise noted.

In the present invention, the "polyethylene glycol fatty acid ester" is a fatty acid ester of a polyethylene glycol which is a fatty acid polymerized with ethylene oxide. Various compounds with different esterified fatty acid are commercially available, and examples include polyethylene glycol monolaurate (NIKKOL MYL-10, Nikko Chemicals Co., Ltd.), polyethylene glycol monostearate (NIKKOL MYS-10V, MYS-25V, MYS-40V, MYS-45V, and MYS-55V, Nikko Chemicals Co., Ltd.), polyethylene glycol monooleate (NIKKOL MYO-6 and MYO-10, Nikko Chemicals Co., Ltd.), polyethylene glycol distearate (NIKKOL CDS-6000P, Nikko Chemicals Co., Ltd.), and polyethylene glycol diisostearate (NIKKOL CDIS-400, Nikko Chemicals Co., Ltd.). These may be used alone or in combination of two or more. In the present invention, the "polyethylene glycol fatty acid ester" includes all of such compounds unless otherwise noted.

In the present invention, the "polyoxyethylene polyoxypropylene glycol" is a compound prepared by addition polymerization of ethylene oxide to the polypropylene glycol which is a polymerized propylene oxide. Various compounds having different average degree of polymerization of the propylene oxide and the ethylene oxide are commercially available, and examples include polyoxyethylene (3) polyoxypropylene (17) glycol (Adeka Pluronic L-31, ADEKA), polyoxyethylene (20) polyoxypropylene (20) glycol (Adeka Pluronic L-44, ADEKA), polyoxyethylene (42) polyoxypropylene (67) glycol (Adeka Pluronic P-123, ADEKA), polyoxyethylene (54) polyoxypropylene (39) glycol (Newdet PE-85, Sanyo Chemical Industries, Ltd.), polyoxyethylene (105) polyoxypropylene (5) glycol (PEP101, Sanyo Chemical Industries, Ltd.), polyoxyethylene (120) polyoxypropylene (40) glycol (Adeka Pluronic F-87, ADEKA), polyoxyethylene (160) polyoxypropylene (30) glycol (Adeka Pluronic F-68, ADEKA), polyoxyethylene (196) polyoxypropylene (67) glycol (Lutrol F127, BASF Japan), and polyoxyethylene (200) polyoxypropylene (70) glycol, and the preferred is polyoxyethylene (105) polyoxypropylene (5) glycol. These may be used alone or in combination of two or more. In the present invention, the "polyoxyethylene polyoxypropylene glycol" includes all of such compounds unless otherwise noted.

In the present invention, the "sucrose fatty acid ester" is an ester of sugar and a fatty acid. Various compounds with different types of the esterified fatty acids and degree of esterification are commercially available, and examples include Surfhope SE PHARMA J-1216 containing 95% of lauric acid in the fatty acid (Mitsubishi-Kagaku Foods Corporation), Surfhope SE PHARMA J-1416 containing 95% of myristic acid in the fatty acid (Mitsubishi-Kagaku Foods Corporation), Surfhope SE PHARMA J-1615 and J-1616 containing 80% of palmitic acid in the fatty acid, (Mitsubishi-Kagaku Foods Corporation), J-1811, J-1815, and J-1816 containing 70% of stearic acid in the fatty acid (Mitsubishi-Kagaku Foods Corporation), and Surfhope SE PHARMA J-1715 containing 70% of oleic acid in the fatty acid, which may be used alone or in combination of two or more. The "sucrose fatty acid ester" used in the present invention include all of such compounds.

The emulsifier added to the self-emulsifying composition of the present invention may have an HLB of at least 10, preferably at least 11, and more preferably at least 12.

Total content of the emulsifier having an HLB of at least 10 in the self-emulsifying composition of the present invention is not particularly limited as long as it is at least 10 parts by weight in relation to 100 parts by weight of the ω3PUFA. The content is typically 10 to 100 parts by weight, preferably 10 to 80 parts by weight, and more preferably 10 to 50 parts by weight in relation to 100 parts by weight of the ω3PUFA.

In the present invention, the "lecithin" is a type of glycerophospholipid, and examples include soybean lecithin, enzymatically decomposed soybean lecithin, hydrogenated soybean lecithin, egg yolk lecithin, hydrogenated phospholipid, phospholipid from milk, lysolecithin, phosphatidyl choline, and phosphatidyl serine. The preferred are soybean lecithin, enzymatically decomposed soybean lecithin, hydrogenated soybean lecithin, and egg yolk lecithin, and the more preferred are soybean lecithin. These may be used alone or in combination of two or more. In the present invention, the "lecithin" includes all of such compounds unless otherwise noted.

Commercially available products include purified soybean lecithin (Nisshin Oilio), purified egg yolk lecithin (Asahi Kasei Pharma Corporation), and egg yolk lecithin PL-100M (Kewpie Corporation), and use of such product is also possible.

In the present invention, the "polyhydric alcohol" is a polyol compound having the structure of a straight chain or cyclic aliphatic hydrocarbon wherein two or more carbon atoms are each substituted with one hydroxy group. Exemplary such polyhydric alcohols include divalent alcohols such as ethyleneglycol, propylene glycol, trimethylene glycol, 1,2-butylene glycol, tetramethylene glycol, 1,3-butylene glycol, 2,3-butylene glycol, and pentamethylene glycol; trivalent alcohols such as glycerin, trimethylolpropane, and 1,2,6-hexane triol, and polyhydric alcohol polymers such as diethylene glycol, dipropylene glycol, triethylene glycol, polyethylene glycol, polypropylene glycol, and polyglycerin, and the preferred are propylene glycol or glycerin. In the present invention, the "polyhydric alcohol" includes all of such compounds unless otherwise noted.

Total amount of the lecithin and the polyhydric alcohol added in the self-emulsifying composition of the present inventionis not particularly limited. However, the total amount of the lecithin and the polyhydric alcohol is typically 0 to 50 parts by weight, preferably 3 to 40 parts by weight, and more preferably 5 to 30 parts by weight in relation to 100 parts by weight of the ω3PUFA.

The ethanol in the self-emulsifying composition of the present invention is preferably used at an amount not causing quality change in the course of capsulation, distribution, or storage, at an amount not causing change in the content of the capsule, and at an amount not exceeding the established upper limit of the daily dose as a drug. The ethanol content is typically up to 10% by weight, preferably up to 4% by weight, more preferably up to 1% by weight, more preferably up to 0.5% by weight, more preferably up to 0.2% by weight, still more preferably up to 0.1% by weight, and most preferably 0% by weight (no ethanol addition).

Preferable ethanol concentration can be adequately determined in consideration of the ω3PUFA concentration in the self-emulsifying composition and the daily dose. When the self-emulsifying composition of the present invention is orally administered at a daily dose in terms of the ω3PUFA of 1800 mg, and for example, the preparation contains 75% by weight of the ω3PUFA, the maximum daily dose of 3.26 mg described in "Dictionary of Drug Additives (in Japanese)" will not be exceeded when the ethanol content is not more than 0.135% by weight.

The preferable embodiment of the self-emulsifying composition of the present invention containing such ω3PUFA and an emulsifier is a combination of EPA-E and/or DHA-E with at least one emulsifier selected from the group consisting of polyoxyethylene hydrogenated castor oil, polyoxyethylene sorbitan fatty acid ester, polyoxyethylene castor oil, sucrose fatty acid ester, and lecithin. When the self-emulsifying composition of the present invention is used as a food such as special purpose food, functional health food, and health food, the preferred is the combination of EPA-E and/or DHA-E with a sucrose fatty acid ester and/or a lecithin which has good results as a food additive. When a sucrose fatty acid ester is used, the preferable amount is 1% by weight to 20% by weight, more preferably 4% by weight to 20% by weight, and most preferably 4% by weight to 10% by weight in the self-emulsifying composition. The most preferable embodiments are a combination of EPA-E and polyoxyethylene (50) hydrogenated castor oil or polyoxyethylene (60) hydrogenated castor oil; a combination of EPA-E and polyoxyethylene (20) sorbitan monooleate; a combination of EPA-E and polyoxyethylene castor oil; and a combination of EPA-E and sucrose fatty acid ester J-1216 or J-1816.

Also preferred is the further combination with a lecithin such as soybean lecithin and/or a polyhydric alcohol such as propylene glycol.

When the emulsifier is at least one member selected from the group consisting of polyoxyethylene hydrogenated castor oil, polyoxyethylene sorbitan fatty acid ester, and polyoxyethylene castor oil, the polyhydric alcohol is preferably a dihydric alcohol, and use of propylene glycol is more preferable. When the emulsifier is a sucrose fatty acid ester, the polyhydric alcohol is preferably a trihydric alcohol, and use of glycerin is more preferable.

Preferably, the composition and therapeutic agent of the present invention is substantially free from water. The "substantially free from water" means that the water content is up to 10% by weight, preferably up to 5% by weight, and even more preferably up to 3% by weight.

The dose and dosage period of the ω3PUFA used in the self-emulsifying composition of the present invention is a dose and period sufficient for realizing the intended action, which may be adequately adjusted depending on the administration route, frequency of administration per day, seriousness of the symptoms, body weight, age, and other factors.

In the case of oral administration, the composition may be administered at a dose in terms of the EPA-E of 0.1 to 5 g/day, preferably 0.2 to 3 g/day, more preferably 0.4 to 1.8 g/day, and most preferably 0.6 to 0.9 g/day in 1 to 3 divided doses. However, the entire dose may be administered at once or in several divided doses. While meal affects absorption of the EPA-E, and the administration of the EPA-E is preferably conducted during the meal or after the meal, and more preferably immediately after the meal (within 30 minutes after the meal), the self-emulsifying composition of the present invention has excellent absorption under fasting, and therefore, it exhibits the intended effects even when administered at a timing other than during, after, or immediately after the meal, for example, before or immediately before the meal or before going to the bed; to patients with reduced absorption ability of the intestinal tract (for example, elderly, patients of intestinal disease, patients after intestinal surgery, terminal cancer patients, or patients taking a lipase inhibitor); or used at a reduced dose.

When orally administered at such dose, the administration period may be adequately determined depending on the target disease and degree of symptoms. For example, in the case of administration to dyslipidemia, the administration period is not particularly limited as long as improvements of biochemical markers related to dyslipidemia, improvement in the pathological conditions or therapeutic effects, and suppression of the progress in metabolic syndrome, cardio- or cerebrovascular event, or ulcer and gangrene of extremities and peripheries are realized. However, administration period is determined to realize the improvements in the concentration of plasma lipid marker (total cholesterol (hereinafter abbreviated as Cho), TG, postprandial TG, low-density lipoprotein Cho, high-density lipoprotein Cho, very-low-density lipoprotein Cho, non-high-density lipoprotein Cho, intermediate-density lipoprotein Cho, very-high-density lipoprotein Cho, free fatty acid, phospholipid, chylomicron, ApoB, lipoprotein(a), remnant-like lipoprotein Cho, small dense low-density lipoprotein Cho, etc.), increase in the skin temperature of extremities and peripheries which can be measured by thermography or the like, increase in the walking distance, increase in the serum CPK or other test value, and improvement of various symptoms such as numbness, coldness, ache, pain at rest, itching, cyanosis, flare, chilblain, neck stiffness, anemia, poor complexion, itching, and crawling. The amelioration or therapeutic effects may be monitored by other biochemical, pathlogical, or symptomatic parameters related to dyslipidemia or peripheral disruption of blood circulation. The administration is preferably continued as long as abnormality is observed in biochemical index such as serum lipid concentration or pathology. In addition, the composition may be administered every alternate day or 2 or 3 days in a week, or as the case may be, a drug withdrawal period of about 1 day to 3 month, and more preferably about 1 week to 1 month may be included.

If indicated by the physician, oral administration may be started at a dose lower than the recommended daily ω3PUFA dose at the first day, and then, the dose may be gradually increased to the maximum daily dose as the maintenance dose. The dose may be reduced depending on the conditions of the patient. Lower daily dose is preferable in view of reducing the side effects, and administration of once or twice a day is preferable in view of the drug compliance.

The self-emulsifying composition of the present invention may also contain additives such as an emulsion aid, stabilizer, antiseptic, surfactant, and antioxidant. Exemplary emulsion aids include fatty acids containing 12 to 22 carbon atoms such as stearic acid, oleic acid, linoleic acid, palmitic acid, linolenic acid, and myristic acid and their salts. Exemplary stabilizers include phosphatidic acid, ascorbic acid, glycerin, and cetanols, and exemplary antiseptics include ethyl paraoxybenzoate and propyl paraoxybenzoate. Exemplary surfactants include sucrose fatty acid esters, sorbitan fatty acid esters, glycerin fatty acid esters, polyglycerin fatty acid esters, polyoxyethylene sorbitan fatty acid esters, polyoxyethylene alkyl ethers, polyoxyethylene fatty acid esters, polyoxyethylene alkyl phenyl ethers, and polyoxyethylene polyoxypropylene alkyl ethers having an HLB of less than 10. Exemplary antioxidants include oil-soluble antioxidants such as butylated hydroxy toluene, butylated hydroxy anisole, propyl gallate, propyl gallate, pharmaceutically acceptable quinone, astaxanthin, and α-tocopherol.

In addition, an adequate carrier or mediater, a colorant, a flavor, and optionally, a vegetable oil or an additive such as non-toxic organic solvent or non-toxic solubilizing agent (for example glycerin), emulsifier, suspending agent (for example, Tween 80 and gum arabic solution), isotonic agent, pH adjusting agent, stabilizer, corrective, flavoring agent, preservative, antioxidant, or absorption promoter commonly used in the art may be adequately combined to prepare an appropriate pharmaceutical preparation.

More specifically, since the ω3PUFA is highly unsaturated, effective amount of an oil-soluble antioxidant, for example, at least one member selected from butylated hydroxytoluene, butylated hydroxyanisole, propyl gallate, propyl gallate, pharmaceutically acceptable quinone, astaxanthin, and α-tocopherol is preferably incorporated in the composition. Storage temperature is preferably room temperature, and frozen storage is preferably avoided since the freezing may result in the loss of self-emulsifying property, dispersibility in the composition, or emulsion stability.

The self-emulsifying composition of the present invention may be administered to the patient orally, endrectally, or transvaginally. However, oral administration is preferable in the case of the patient who can take the drug orally, and the composition may be administered in the form of a jelly preparation in the case of patients undergoing dialysis or patients with aphagia by jelling the composition with gelatin or the like.

The self-emulsifying composition of the present invention can be produced by mixing the ω3PUFA, the emulsifier having an HLB of at least 10, and the optionally added components such as lecithin, polyhydric alcohol, and antioxidant with optional heating to dissolve the components.

The self-emulsifying composition of the present invention may be used by combining with a second effective component. The second effective component may be adequately determined depending on the target disease and the seriousness of the symptom. However, the second effective component is preferably a component that does not adversely affect the effects of the ω3PUFA, and examples include therapeutic agent for hyperlipidemia, antihypertensives, antidiabetics, antioxidants, blood flow improving agents, and bile acid derivatives.

Of the preferable examples of the second effective component, exemplary therapeutic agents for hyperlipidemia include polyenephosphatidylcholine, unsaponifiable soybean oil (soy sterol), gamma-oryzanol, riboflavin butyrate, dextran sulfate sodium sulfur 18, pantethine, and elastase; statins such as pravastatin, simvastatin, atorvastatin, fluvastatin, pitavastatin, rosuvastatin, and cerivastatin; fibrates such as simfibrate, clofibrate, clinofibrate, bezafibrate, and fenofibrate; lipolytic enzyme inhibitors such as orlistat and cetilistat; resins such as colestyramine and colestimide; and ezetimibe.

Exemplary antihypertensives include angiotensin II receptor blockers such as irbesartan, olmesartan medoxomil, candesartan cilexetil, telmisartan, valsartan, and losartan potassium; angiotensin-converting enzyme inhibitors such as alacepril, imidapril hydrochloride, enalapril maleate, captopril, quinapril hydrochloride, cilazapril hydrate, temocapril hydrochloride, delapril hydrochloride, trandolapril, benazepril hydrochloride, perindopril, and lisinopril hydrate; calcium antagonists such as azelnidipine, amlodipine besylate, aranidipine, efonidipine hydrochloride, cilnidipine, nicardipine hydrochloride, nifedipine, nimodipine, nitrendipine, nilvadipine, barnidipine hydrochloride, felodipine, benidipine, and manidipine; α receptor blocker such as tolazoline, and phentolamine; β receptor blockers such as atenolol, metoprolol, acebutolol, propranolol, pindolol, carvedilol, and labetalol hydrochloride; α receptors stimulant such as clonidine and methyldopa; and diuretics such as eplerenone, hydrochlorothiazide, and furosemide.

Exemplary antidiabetics include α-glucosidase inhibitors such as acarbose, voglibose, and miglitol; sulfonyl urea hypoglycemics such as gliclazide, glibenclamide, glimepiride, and tolbutamide; fast-acting insulin secretagogues such as nateglinide and mitiglinide; biguanide hypoglycemics such as metformin hydrochloride and buformin hydrochloride; dipeptidyl phosphatase 4 inhibitors such as sitagliptin, vildagliptin, alogliptin, and saxagliptin; thiazolidine reagents such as pioglitazone hydrochloride and rosiglitazone maleate; and glucagon-like peptide 1 derivative reagents such as exenatide and liraglutide.

Exemplary antioxidants include vitamins such as ascorbic acid (vitamin C), tocopherol (vitamin E), and tocopherol nicotinate, and N-acetylcysteine, probucol.

Exemplary blood flow improving agents include cilostazol, ticlopidine hydrochloride, alprostadil, limaprost, beraprost sodium, sarpogrelate hydrochloride, argatroban, naftidrofuryl, isoxsuprine hydrochloride, batroxobin, dihydroergotoxine mesilate, tolazoline hydrochloride, hepronicate, and shimotsu-to extract.

Exemplary bile acid derivatives include ursodeoxycholic acid, chenodeoxycholic acid, bile powder, deoxycholic acid, cholic acid, bile extract, bear bile, oriental bezoar, and dehydrocholic acid. Preferable examples also include biotin (vitamin B7), cyanocobalamin (vitamin B12), pantothenic acid (vitamin B5), folic acid (vitamin B9), thiamine (vitamin B1), vitamin A, vitamin D, vitamin K, tyrosine, pyridoxine (vitamin B6), branched chain amino acids such as leucine, isoleucine, and valine, calcium, iron, zinc, copper, and magnesium. Other examples include components used in designated health foods and functional nutritional foods such as soy protein, chitosan, low molecular weight sodium alginate, dietary fiber from psyllium seed coat, soy peptide with bound phospholipids, phytosterol ester, plant stanol ester, diacylglycerol, globin digest, and tea catechin.

The self-emulsifying composition of the present invention may preferably have at least one of the effects including excellent self-emulsifying property, excellent dispersibility in the composition, excellent emulsion stability, excellent storage stability, excellent absorption property, and in particular, excellent absorption property and rate under fasting, and excellent convenience or compliance for the patients so that the composition can exhibit pharmacological effect of the ω3PUFA.

The self-emulsifying composition of the present invention can be used as a therapeutic agent for various diseases of animals, and in particular, mammals, for example, therapeutic agent for dyslipidemia, therapeutic agent for postprandial hypertriglyceridemia, anti-arteriosclerosis agent, platelet aggregation suppressant, therapeutic agent for peripheral circulatory insufficiency, therapeutic agent for inflammatory diseases, anticancer agent, and therapeutic agent for central disease. The self-emulsifying composition of the present invention is particularly effective for amelioration, treatment, or secondary prevention of dyslipidemia and postprandial hypertriglyceridemia, or prevention of the progress of the metabolic syndrome, cardio- or cerebrovascular event, or ulcer and gangrene of extremities and peripherie. Exemplary mammals include human, domestic animals such as cow, horse, and pig, and companion animals such as dog, cat, rabbit, rat, and mouse, and the preferred is human. The self-emulsifying composition of the present invention is particularly expected to exhibit amelioration or therapeutic effects for dyslipidemia and postprandial hypertriglyceridemia in dyslipidemia patients such as metabolic syndrome patients experiencing increase in blood lipid, expression of insulin resistance, or increase in blood pressure. The self-emulsifying composition of the present invention can reduce burden of the patients by reducing the dose and daily frequency of the administration, and hence, by improving the drug compliance. This also results in the higher effects of amelioration or treatment.

EXAMPLES

Next, the present invention is described in further detail by referring to the following Examples which by no means limit the scope of the invention.

Example 1

0.5 g of soybean lecithin, 1.0 g of polyoxyethylene (60) hydrogenated castor oil, 0.4 g of propylene glycol, and 3.1 g of EPA-E were weighed, and mixed while heating to a temperature of about 70° C. to prepare a self-emulsifying composition. After substituting with nitrogen, the self-emulsifying composition was hermetically sealed and stored at room temperature until the evaluation. Formulation of the self-emulsifying composition is shown in Table 1.

TABLE 1

| Ingredients | Formulation (% by weight) |
|---|---|
| EPA-E | 62.0 |
| Soybean lecithin | 10.0 |
| Polyoxyethylene (60) hydrogenated castor oil | 20.0 |
| Propylene glycol | 8.0 |
| Total | 100.0 |

Example 2

0.5 g of soybean lecithin, 1.0 g of polyoxyethylene (50) hydrogenated castor oil, 0.4 g of propylene glycol, and 3.1 g of EPA-E were weighed, and a self-emulsifying composition was prepared and stored by repeating the procedure of Example 1. Formulation of the self-emulsifying composition is shown in Table 2.

TABLE 2

| Ingredients | Formulation (% by weight) |
|---|---|
| EPA-E | 62.0 |
| Soybean lecithin | 10.0 |
| Polyoxyethylene (50) hydrogenated castor oil | 20.0 |
| Propylene glycol | 8.0 |
| Total | 100.0 |

Example 3

0.5 g of soybean lecithin, 0.9 g of polyoxyethylene castor oil, 0.6 g of propylene glycol, and 3.0 g of EPA-E were weighed, and a self-emulsifying composition was prepared and stored by repeating the procedure of Example 1. Formulation of the self-emulsifying composition is shown in Table 3.

TABLE 3

| Ingredients | Formulation (% by weight) |
|---|---|
| EPA-E | 60.0 |
| Soybean lecithin | 10.0 |
| Polyoxyethylene castor oil | 18.0 |
| Propylene glycol | 12.0 |
| Total | 100.0 |

Example 4

0.6 g of soybean lecithin, 0.6 g of polyoxyethylene (60) hydrogenated castor oil, 0.5 g of propylene glycol, and 3.3 g of EPA-E were weighed, and a self-emulsifying composition was prepared and stored by repeating the procedure of Example 1. Formulation of the self-emulsifying composition is shown in Table 4.

TABLE 4

| Ingredients | Formulation (% by weight) |
|---|---|
| EPA-E | 66.0 |
| Soybean lecithin | 12.0 |
| Polyoxyethylene (60) hydrogenated castor oil | 12.0 |
| Propylene glycol | 10.0 |
| Total | 100.0 |

Example 5

0.5 g of soybean lecithin, 0.5 g of polyoxyethylene (50) hydrogenated castor oil, 0.5 g of propylene glycol, and 3.5 g of EPA-E were weighed, and a self-emulsifying composition was prepared and stored by repeating the procedure of Example 1. Formulation of the self-emulsifying composition is shown in Table 5.

TABLE 5

| Ingredients | Formulation (% by weight) |
|---|---|
| EPA-E | 70.0 |
| Soybean lecithin | 10.0 |
| Polyoxyethylene (50) hydrogenated castor oil | 10.0 |
| Propylene glycol | 10.0 |
| Total | 100.0 |

Example 6

0.3 g of soybean lecithin, 0.3 g of polyoxyethylene (20) sorbitan monooleate, 0.9 g of polyoxyethylene (60) hydrogenated castor oil, 0.4 g of propylene glycol, and 3.1 g of EPA-E were weighed, and a self-emulsifying composition was prepared and stored by repeating the procedure of Example 1. Formulation of the self-emulsifying composition is shown in Table 6.

TABLE 6

| Ingredients | Formulation (% by weight) |
|---|---|
| EPA-E | 62.0 |
| Soybean lecithin | 6.0 |
| Polyoxyethylene (20) sorbitan monooleate | 6.0 |
| Polyoxyethylene (60) hydrogenated castor oil | 18.0 |
| Propylene glycol | 8.0 |
| Total | 100.0 |

Example 7

2.0 g of polyoxyethylene (20) sorbitan monooleate, 0.35 g of sorbitan sesquioleate, and 2.65 g of EPA-E were weighed, and a self-emulsifying composition was prepared and stored by repeating the procedure of Example 1. Formulation of the self-emulsifying composition is shown in Table 7.

TABLE 7

| Ingredients | Formulation (% by weight) |
|---|---|
| EPA-E | 53.0 |
| Polyoxyethylene (20) sorbitan monooleate | 40.0 |
| Sorbitan sesquioleate | 7.0 |
| Total | 100.0 |

Example 8

0.5 g of soybean lecithin, 0.9 g of polyoxyethylene (40) hydrogenated castor oil, 0.6 g of propylene glycol, and 3.0 g of EPA-E were weighed, and a self-emulsifying composition was prepared and stored by repeating the procedure of Example 1. Formulation of the self-emulsifying composition is shown in Table 8.

TABLE 8

| Ingredients | Formulation (% by weight) |
|---|---|
| EPA-E | 60.0 |
| Soybean lecithin | 10.0 |
| Polyoxyethylene (40) hydrogenated castor oil | 18.0 |
| Propylene glycol | 12.0 |
| Total | 100.0 |

Example 9

27.0 g of soybean lecithin, 21.0 g of polyoxyethylene (20) sorbitan monooleate, 30.0 g of polyoxyethylene castor oil, 27.0 g of propylene glycol, and 195.0 g of EPA-E were weighed, and a self-emulsifying composition was prepared and stored by repeating the procedure of Example 1. Formulation of the self-emulsifying composition is shown in Table 9.

TABLE 9

| Ingredients | Formulation (% by weight) |
|---|---|
| EPA-E | 65.0 |
| Soybean lecithin | 9.0 |
| Polyoxyethylene (20) sorbitan monooleate | 7.0 |
| Polyoxyethylene castor oil | 10.0 |
| Propylene glycol | 9.0 |
| Total | 100.0 |

Example 10

1.2 g of enzymatically decomposed soybean lecithin, 1.2 g of Surfhope SE PHARMA J-1216 (Mitsubishi-Kagaku Foods Corporation), and 5.1 g of concentrated glycerin were weighed, and mixed until the mixture became homogeneous with heating to a temperature of about 80° C. Next, 22.5 g of EPA-E was gradually added to the mixture with stirring to prepare a self-emulsifying composition. After substituting with nitrogen, the self-emulsifying composition was hermetically sealed and stored at room temperature until the evaluation. Formulation of the self-emulsifying composition is shown in Table 10.

TABLE 10

| Ingredients | Formulation (% by weight) |
|---|---|
| EPA-E | 75.0 |
| Enzymatically decomposed soybean lecithin | 4.0 |
| Surfhope SE PHARMA J-1216 | 4.0 |
| Concentrated glycerin | 17.0 |
| Total | 100.0 |

Example 11

24.0 g of Surfhope SE PHARMA J-1216 and 51.0 g of concentrated glycerin were weighed, and mixed until the mixture became homogeneous with heating to a temperature of about 80° C. Next, 225.0 g of EPA-E was gradually added to the mixture with stirring to prepare a self-emulsifying composition. After substituting with nitrogen, the self-emulsifying composition was hermetically sealed and stored at room temperature until the evaluation. Formulation of the self-emulsifying composition is shown in Table 11.

TABLE 11

| Ingredients | Formulation (% by weight) |
|---|---|
| EPA-E | 75.0 |
| Surfhope SE PHARMA J-1216 | 8.0 |
| Concentrated glycerin | 17.0 |
| Total | 100.0 |

Example 12

24.0 g of Surfhope SE PHARMA J-1816 (Mitsubishi-Kagaku Foods Corporation) and 51.0 g of concentrated glycerin were weighed, and mixed until the mixture became homogeneous with heating to a temperature of about 80° C.

A self-emulsifying composition was prepared and stored as in the case of Example 11. Formulation of the self-emulsifying composition is shown in Table 12.

TABLE 12

| Ingredients | Formulation (% by weight) |
|---|---|
| EPA-E | 75.0 |
| Surfhope SE PHARMA J-1816 | 8.0 |
| Concentrated glycerin | 17.0 |
| Total | 100.0 |

Example 13

15.0 g of soybean lecithin, 21.0 g of Surfhope SE PHARMA J-1216, and 39.0 g of concentrated glycerin were weighed, and mixed until the mixture became homogeneous with heating to a temperature of about 80° C. A self-emulsifying composition was prepared and stored as in the case of Example 11. Formulation of the self-emulsifying composition is shown in Table 13.

TABLE 13

| Ingredients | Formulation (% by weight) |
|---|---|
| EPA-E | 75.0 |
| Soybean lecithin | 5.0 |
| Surfhope SE PHARMA J-1216 | 7.0 |
| Concentrated glycerin | 13.0 |
| Total | 100.0 |

Comparative Example 1

1.5 g of soybean lecithin, 0.4 g of propylene glycol, and 3.1 g of EPA-E were weighed, and a composition was prepared and stored by repeating the procedure of Example 1. Formulation of the composition is shown in Table 14.

TABLE 14

| Ingredients | Formulation (% by weight) |
|---|---|
| EPA-E | 6.0 |
| Soybean lecithin | 30.0 |
| Propylene glycol | 8.0 |
| Total | 100.0 |

Comparative Example 2

0.13 g of soybean lecithin, 0.3 g of polyoxyethylene (20) sorbitan monooleate, 0.22 g of absolute ethanol, and 4.35 g of EPA-E were weighed, and a composition was prepared. After substituting with nitrogen, the composition was hermetically sealed and stored at room temperature until the evaluation. Formulation of the composition is shown in Table 15.

TABLE 15

| Ingredients | Formulation (% by weight) |
|---|---|
| EPA-E | 87.0 |
| Soybean lecithin | 2.0 |
| Polyoxyethylene (20) sorbitan monooleate | 6.0 |
| Absolute ethanol | 4.0 |
| Total | 100.0 |

Experimental Example 1

Evaluation of Self-Emulsifying Property

The self-emulsifying compositions of the Examples 1 to 8 and 10 to 13 and the compositions of Comparative Example 1 and 2 were evaluated for their self-emulsifying property by dropping 0.05 g of each composition to 7 ml of purified water at 37° C. in test tube. The result was evaluated "good" when the composition emulsified merely by dropping, and "fail" when the composition failed to undergo natural emulsification merely by the dropping. Next, the mixture was lightly stirred under the same conditions for all compositions to evaluate their conditions. The dispersibility of the composition was evaluated "good" when the composition was dispersed, and "fail" when a part of the composition remained non-dispersed as a mass. The emulsion stability was evaluated "good" when separation of the oil content was not observed, and "fail" when such separation of the oil content was observed. In the case of Comparative Example 1, the emulsion stability was not evaluated since the composition was not emulsified. Table 16 shows the results of the evaluation.

TABLE 16

| | Self-emulsifying property | Dispersibility of the composition | Emulsion stability |
|---|---|---|---|
| Example 1 | good | good | good |
| Example 2 | good | good | good |
| Example 3 | good | good | good |
| Example 4 | good | good | good |
| Example 5 | good | good | good |
| Example 6 | good | good | good |
| Example 7 | good | good | good |
| Example 8 | good | good | good |
| Example 10 | good | good | good |
| Example 11 | good | good | good |
| Example 12 | good | good | good |
| Example 13 | good | good | good |
| Comparative Example 1 | fail | fail | not determined |
| Comparative Example 2 | good | good | fail |

In the case of the self-emulsifying composition of the Examples 1 to 8 and 10 to 13, the results were favorable for all of the self-emulsifying property, the dispersibility of the composition, and the emulsion stability. The composition of Comparative Example 1 was not emulsified, and the composition of Comparative Example 2 was insufficient in emulsion stability while it exhibited good self-emulsifying property and dispersibility. The result that the self-emulsifying composition of the present invention could be used as a self-emulsifying preparation with good emulsion stability indicates improvement of the absorption in the case of the oral administration. In addition, the compositions of the Examples 1 to 13 are expected to be usable as praparations free from the problems caused by the ethanol inclusion since ethanol is not used in these compositions.

Experimental Example 2

Pharmacokinetics in Beagle

The compositions of the Examples 6, 7, 9, 10, 13, and Comparative Example 2 were orally administered to 3 to 8 male beagles (34 to 45 months old having a body weight of 11 to 17 kg, Kitayama Labes Co., Ltd.) under fasting, and time course blood EPA concentration was evaluated. The test animals were fasted at least for 18 hours before the test, and each animal was administered with the composition at an amount of 600 mg in terms of the EPA-E. The blood was collected before the administration and at 1, 1.5, 2, 2.5, 3, 4, 6, 8, and 24 hours after the administration, and after separating and treating the plasma, plasma EPA concentration was measured by LC/MS/MS. The EPA-E stock solution filled in a capsule was also administered to the control group animals. Table 17 shows maximum blood concentration (Cmax), area under the curve of the blood concentration from 0 hour to 2 hours ($AUC_{0-2}$), and area under the curve of the blood concentration from 0 hour to 24 hours ($AUC_{0-24}$) calculated from the test results. In calculating each parameter, the value was corrected by subtracting the blood EPA concentration before the administration from the blood concentration after the administration.

TABLE 17

| | Cmax (µg/mL) | $AUC_{0-2}$ (µg/mL · hr) | $AUC_{0-24}$ (µg/mL · hr) |
|---|---|---|---|
| Example 6 | 73.7 | 90.8 | 522.8 |
| Example 7 | 78.8 | 84.7 | 559.0 |
| Example 9 | 64.7 | 63.7 | 542.4 |
| Example 10 | 82.6 | 79.5 | 496.5 |
| Example 13 | 67.5 | 54.3 | 471.6 |
| Comparative Example 2 | 26.8 | 21.0 | 358. |
| EPA-E stock solution (control) | 16.6 | 14.4 | 188.0 |

The animals administered with the self-emulsifying compositions of the Examples 6, 7, 9, 10, and 13 exhibited the values of Cmax and $AUC_{0-2}$ which are the parameter of absorption rate higher than the animals administered with the control group or the Comparative Examples. More specifically, the $AUC_{0-2}$ which is a parameter indicating the increase of blood concentration immediately after the administration was about 3.8 to 6.3 times higher in the animals administered with the composition of the Examples compared to the animals of the control group, and about 2.6 to 4.3 times higher in the animals administered with the composition of the Examples compared to the animals administered with the composition of the Comparative Example 2. Similarly, the Cmax value was about 3.9 to 5.0 times higher in the animals administered with the composition of the Examples compared to the animals of the control group, and about 2.4 to 3.1 times higher in the animals administered with the composition of the Comparative Example 2. In the meanwhile, the $AUC_{0-24}$ which is the parameter for the absorption amount was about 2.5 to 3.0 times higher in the animals administered with the composition of the Examples compared to the animals of the control group, and about 1.3 to 1.6 times higher in the animals administered with the composition of the Comparative Example 2. As described above, in the animals administered with the self-emulsifying compositions of the Examples, not only the amount of EPA absorbed in the 24 hours after the oral administration but also the absorption immediately after the administration increased compared to the animals of the control group and animals administered with the composition of the comparative Example. Accordingly, the self-emulsifying composition of the present invention is expected to serve a self-emulsifying preparation which realizes faster and larger increase in blood EPA concentration, and hence, more rapid and effective pharmacological action even when administered under fasting such as before the meal or before going to bed.

Experimental Example 3

Pharmacokinetics in Cynomolgus Monkey

The compositions of the Example 6 was orally administered to 6 cynomolgus monkies (2 to 5 years having a body weight of 2.70 to 4.65 kg, Hamri Co., Ltd.) under fasting, and time course blood EPA concentration was evaluated. The test animals were fasted at least for 12 hours before the test, and each animal was administered with the self-emulsifying composition at an amount of 4.5 mg/kg in terms of the EPA-E. The EPA-E stock solution filled in a capsule was also administered to the control group animals. The blood was collected before the administration and at 1, 2, 4, 6, 8, 10, 12, 24, 48, and 72 hours after the administration, and after separating and treating the plasma, plasma EPA was measured by LC/MS/MS. Table 18 shows maximum blood concentration (Cmax), area under the curve of the blood concentration from 0 hour to 12 hours ($AUC_{0-12}$), and area under the curve of the blood concentration from 0 hour to 72 hours ($AUC_{0-72}$) calculated from the test results. In calculating each parameter, the value was corrected by subtracting the blood EPA concentration before the administration from the blood concentration after the administration.

TABLE 18

| | Cmax (µg/mL) | $AUC_{0-12}$ (µg/mL · hr) | $AUC_{0-72}$ (µg/mL · hr) |
|---|---|---|---|
| Example 6 | 71.4 | 510.4 | 1688.8 |
| EPA-E stock solution (control) | 7.4 | 46.5 | 284.5 |

The animals administered with the composition of the Example 6 experienced increase in all of the blood concentration parameters compared to the animals of the control group, and in the case of Cmax and $AUC_{0-12}$, the values increased about 10 fold. More specifically, administration of the self-emulsifying composition of Example 6 was confirmed to result not only in the increase of the absorbed amount, but also, in the immediate EPA absorption after the oral administration. Accordingly, the self-emulsifying composition of the present invention is expected to serve a self-emulsifying preparation which realizes faster and larger increase in the blood EPA concentration, and hence, more rapid and effective pharmacological action even when administered under fasting such as before the meal or before going to bed.

Experimental Example 4

Effectiveness in Fasted Glucose Tolerance Model Rat

Male Sprague Dawley rats (10 week old, Charles River Laboratories Japan, Inc.) are divided into 4 groups each comprising 10 animals with even body weight and serum TG value. Control group is administered with olive oil, EPA-E group is administered with EPA-E stock solution, Example group is administered with the self-emulsifying composition of Example 6, and comparative group is administered with the composition of Comparative Example 2 by filling in the gelatin capsule and perorally administering the capsule to the animals, respectively. The test animals are fasted at least 24 hours before the administration, and each animal is administered with the composition at an amount of 100 mg/kg in terms of the olive oil or the EPA-E. 30 minutes after the administration, glucose solution in physiological saline is orally administered at 2 g/kg. Blood is periodically collected from tail vein, and plasma TG concentration and free fatty acid concentration are measured by using a commercially available assay kit. Change from the value before the glucose loading is calculated for each parameter.

In the control group, plasma TG concentration increases after the glucose loading, and suppressive effect for this increase is not observed in the group administered with the EPA-E. However, increase in the plasma TG concentration and free fatty acid concentration after the glucose loading is suppressed in the Example group and the Comparative Example group, and the suppression effect is superior in the Example group compared to the Comparative Example group.

Accordingly, the self-emulsifying compositions of the present invention is useful in improving or treating the postprandial hypertriglyceridemia and postprandial hyper free fatty acidemia by the administration before the meal.

(Preparation Example 1) Self Emulsifying Capsule Preparation

The self-emulsifying compositions produced in Examples 1 to 7 at an amount of 200 mg in terms of EPA-E are encapsulated in a soft gelatin capsule or a hard gelatin capsule to prepare a self-emulsifying capsule. Self emulsifying capsules are also prepared by encapsulating the self-emulsifying compositions produces in Examples 1 to 7 together with a tocopherol at a final concentration of 0.2% in the capsule.

(Preparation Example 2) Self Emulsifying Capsule Preparation

The procedure of Examples 1 to 7 is repeated by replacing EPA-E with ω3PUFA (Lovaza (registered trade mark) (K85EE) containing about 90% of ωPUFA and about 84% of EPA-E+DHA-E, EPA-E:DHA-E=about 1.2:1) to prepare self-emulsifying compositions. These self-emulsifying compositions at an amount of 200 mg in terms of the ωPUFA are encapsulated in a soft gelatin capsule or a hard gelatin capsule to prepare a self-emulsifying capsule. Self emulsifying capsules are also prepared by encapsulating the self-emulsifying composition together with a tocopherol at a final concentration of 0.2% in the capsule.

(Preparation Example 3) Blended Self-Eemulsifying Capsule Preparation

The procedure of the Example 6 is repeated by further adding 1.0 g of tocopherol nicotinate and/or 0.4 g of ursodeoxycholic acid to the composition of the Example 6 to thereby produce a self-emulsifying composition. The self-emulsifying composition at an amount of 200 mg in terms of the EPA-E is encapsulated in a soft gelatin capsule or a hard gelatin capsule to prepare a self-emulsifying capsule.

(Preparation Example 4) Self Emulsifying Capsule Preparation

A soft gelatin capsule is prepared by rotary method by filling the capsule with 200 mg of the self-emulsifying composition of Example 9. The self-emulsifying capsule prepared by this method exhibit a shape similar to the soft gelatin capsule filled solely with the EPA-E, and deformation of the capsule film is not recognized.

INDUSTRIAL APPLICABILITY

The self-emulsifying composition of the present invention is capable of providing a self-emulsifying composition which has at least one of excellent self-emulsifying property, dispersibility in the composition, emulsion stability, and absorption property, and in particular, oral absorption property and rate under fasting even though the composition contains no ethanol or has a low ethanol concentration by adding an emulsifier having an HLB of at least 10 to at least one member selected from ω3PUFA and homogenating the mixture. Also provided a drug of such self-emulsifying composition, its production method, and a method for its use.

The self-emulsifying composition of the present invention which can be more rapidly absorbed even in the case of oral administration under fasting compared to conventional compositions is expected to show preventive and therapeutic effects of the ω3PUFA. More specifically, the self-emulsifying composition of the present invention shows its effectiveness by the administration of 1 to 2 times a day at non-limited timing, namely, without the limitation of the administering three times a day immediately after the meal, and this convenience for the patients leads to the improved drug compliance, and hence, further improvement in the effectiveness. In addition, the self-emulsifying composition of the present invention can be combined with a drug which is administered not by the administration immediately after the meal, and also, a drug which is a combination with such drug may also be produced. Furthermore, the self-emulsifying composition of the present invention shows various clinical merits such as suppression of the serum TG increase after the meal by administering the composition before the meal and prevention of essential fatty acid deficiency associated with lipase inhibitor administration by administration of the composition before going to the bed.

Compared to the conventional emulsion preparation, the self-emulsifying composition of the present invention can be produced, delivered, and stored at reduced cost and with less trouble. In addition, the self-emulsifying composition of the present invention can be prepared water-free with higher concentration of the effective components, and hence, at reduced preparation volume, and this enables administration of the composition to patients with water intake restriction. Furthermore, the self-emulsifying composition of the present invention can be encapsulated in a gelatin capsule and the like, and this is expected to improve both drug convenience and drug compliance.

Due to the non-inclusion or reduced inclusion of the ethanol in the self-emulsifying composition of the present invention, this composition has reduced risk of capsule deformation and bubble entrapment by the ethanol volatilization during the capsulation step, and in particular, during the drying step, and also, reduced risk of capsule deformation and crack generation by the ethanol volatilization during the distribution and storage process. This composition also has reduced risk of the denaturing such as clouding and separation of the capsule content by the ethanol volatilization. Furthermore, side effects of the ethanol is absent or reduced in alcohol (ethanol) intolerant patients, and it is expected that the composition can be safely administered for a long period.

What is claimed:

1. A method for increasing plasma ω3 polyunsaturated fatty acids (ω3PUFA) concentration comprising:
   administering to a subject in need thereof a self-emulsifying composition comprising
   (a) 5 to 50% by weight of an emulsifier having an HLB of at least 10, wherein the emulsifier is at least one member selected from the group consisting of polyoxyethylene hydrogenated castor oil, polyoxyethylene sorbitan fatty acid ester, polyoxyethylene castor oil, polyethylene glycol fatty acid ester, polyoxyethylene polyoxypropylene glycol, sucrose fatty acid ester;
   (b) 50 to 95% by weight in total of at least one compound selected from the group consisting of ω3PUFA and pharmaceutically acceptable salts and esters thereof;
   (c) ethanol is in an amount up to 4% by weight in relation to the total content of the compound and the emulsifier; and
   (d) 3 to 40 parts by weight of a lecithin based on 100 parts by weight of component (b).

2. The method according to claim 1, wherein the composition does not contain ethanol.

3. The method according to claim 1, wherein the emulsifier is at least one member selected from the group consisting of polyoxyethylene hydrogenated castor oil, polyoxyethylene sorbitan fatty acid ester, polyoxyethylene castor oil, and sucrose fatty acid ester.

4. The method according to claim 1, wherein the polyoxyethylene hydrogenated castor oil is at least one member selected from the group consisting of
   polyoxyethylene (20) hydrogenated castor oil,
   polyoxyethylene (40) hydrogenated castor oil,
   polyoxyethylene (50) hydrogenated castor oil,
   polyoxyethylene (60) hydrogenated castor oil, and
   polyoxyethylene (100) hydrogenated castor oil.

5. The method according to claim 1, wherein the polyoxyethylene sorbitan fatty acid ester is at least one member selected from the group consisting of polyoxyethylene sorbitan monooleate, polyoxyethylene sorbitan tristearate, polyoxyethylene sorbitan monostearate, polyoxyethylene sorbitan monopalmitate, and polyoxyethylene sorbitan monolaurate.

6. The method according to claim 1, wherein the sucrose fatty acid ester is at least one member selected from the group consisting of sucrose laurate, sucrose myristate, sucrose palmitate, sucrose stearate, and sucrose oleate.

7. The method according to claim 1, wherein the lecithin is at least one member selected from the group consisting of soybean lecithin, enzymatically decomposed soybean lecithin, hydrogenated soybean lecithin, and egg yolk lecithin.

8. The method according to claim 1, wherein the composition contains a polyhydric alcohol.

9. The method according to claim 8, wherein the polyhydric alcohol is propylene glycol or glycerin.

10. The method according to claim 1, wherein the composition contains at least one member selected from the group consisting of eicosapentaenoic acid, docosahexaenoic acid, and their pharmaceutically acceptable salts and esters.

11. The method according to claim 1, wherein the composition contains ethyl icosapentate and/or ethyl docosahexaenoate.

12. The method according to claim 1, wherein total content of the emulsifier having an HLB of at least 10 is 10 to 100 parts by weight in relation to 100 parts by weight of the at least one compound selected from the group consisting of ω3 polyunsaturated fatty acids and their pharmaceutically acceptable salts and esters.

13. The method according to claim 1, wherein total content of the emulsifier having an HLB of at least 10 is 10 to 50 parts by weight in relation to 100 parts by weight of the at least one compound selected from the group consisting of ω3 polyunsaturated fatty acids and their pharmaceutically acceptable salts and esters.

* * * * *